United States Patent
Jacquet et al.

(10) Patent No.: US 8,561,488 B2
(45) Date of Patent: Oct. 22, 2013

(54) ON-LINE PRODUCTION PROCESS OF SAND PRESENTING A CONTROLLED METHYLENE BLUE VALUE

(75) Inventors: Alain Jacquet, Saint Didier de Formans (FR); Laurence Martin, L'Isle d'Abeau (FR); Stephane Brocas, Montpellier (FR); Hakimi Yahiaoui, Saint Priest (FR)

(73) Assignee: Lafarge, Paris (FR)

( * ) Notice: Subject to any disclaimer, the term of this patent is extended or adjusted under 35 U.S.C. 154(b) by 819 days.

(21) Appl. No.: 12/442,880

(22) PCT Filed: Sep. 25, 2007

(86) PCT No.: PCT/FR2007/001561
§ 371 (c)(1),
(2), (4) Date: Mar. 25, 2009

(87) PCT Pub. No.: WO2008/037891
PCT Pub. Date: Apr. 3, 2008

(65) Prior Publication Data
US 2009/0241696 A1    Oct. 1, 2009

(30) Foreign Application Priority Data
Sep. 26, 2006    (FR) ...................... 06 08419

(51) Int. Cl.
*G01N 33/00* (2006.01)
(52) U.S. Cl.
USPC ........................................................ 73/866
(58) Field of Classification Search
None
See application file for complete search history.

(56) References Cited

U.S. PATENT DOCUMENTS

| | | | | |
|---|---|---|---|---|
| 2,814,204 A | * | 11/1957 | Moyle, Jr. | 73/863.92 |
| 5,168,083 A | * | 12/1992 | Matthews et al. | 501/146 |
| 5,932,191 A | * | 8/1999 | Chevallier et al. | 424/52 |

FOREIGN PATENT DOCUMENTS

WO    WO 01/53607 A2    7/2001

OTHER PUBLICATIONS

International Search Report dated Feb. 5, 2008 for PCT/FR2007/001561.
"Ein neues Konzept zur Brechsand-Erzeugung"; Metso Minerals; Metso Minerals Kundeninformationen; Aggregates news, No. 5., 2003; pp. 1-2; XP002444610.
"EN 933-9: Prüfverfahren für geometrische Eigenschaften von Gesteinskörnungen; Teil 9; Beurteilung von Feinanteilen—Methylenblau-Verfahren"; Normes, Oct. 1998; XP008081756.
"En 12620: Gesteinskörnungen für Beton"; Normes; Sep. 2002; XP008081634.
"L'essai au bleu de methylene turbidimetrique"; Tran Ngoc Lan et al; Bulletin de l'Association Internationale de Geologie De L'Ingenieur; No. 29; 1984; pp. 453-456; XP002444609.

* cited by examiner

*Primary Examiner* — Robert R Raevis
(74) *Attorney, Agent, or Firm* — Pillsbury Winthrop Shaw Pittman, LLP

(57) ABSTRACT

An embodiment of the invention provides a production process of sand including the extraction of sand from a quarry; the periodic, on-line and automated withdrawal of a sample of sand; and the automated measurement of the methylene blue value on the sample of sand. Another embodiment of the invention provides a production line of sand including means of extraction of sand from a quarry; periodic and automated means of withdrawal of a sample of sand; and automated means of measuring the methylene blue value for the sample of sand.

32 Claims, 1 Drawing Sheet

ON-LINE PRODUCTION PROCESS OF SAND PRESENTING A CONTROLLED METHYLENE BLUE VALUE

CROSS-REFERENCE TO RELATED APPLICATIONS

This is the U.S. National Stage of PCT/FR2007/001561, filed Sep. 25, 2007, which in turn claims priority to French Patent Application No. 0608419, filed Sep 26, 2006, the entire contents of both applications are incorporated herein by reference in their entireties.

DOMAINE OF THE INVENTION

The present invention pertains to an on-line production process of sand presenting a controlled methylene blue value as well as an associated production line and a measurement process of the methylene blue value specially adapted to the said sand production process.

TECHNICAL BACKGROUND

Ready-mix concretes meet specific formulation criteria that require using sands presenting a certain number of characteristics in order to be used in this application. Among these characteristics there is one that is essential, this is the cleanliness of the sands. The cleanliness is related to the amount of noxious impurities for a given application. The latter may be of various types but the most noxious impurities are clays.

Indeed, the nature and level of clays in the sands influences the workability characteristics of the concretes. Now, on worksites, workers generally work at a constant workability level. Consequently, the presence of clays in the sands requires modifications of the formulation. The correction is possible by adding admixtures or water. Nonetheless, the addition of admixtures represents an important cost. Furthermore, if the admixture is a retarder, the correction with the admixture is only obtained to a certain degree. As for the addition of water, it is problematic because it induces a drop of the hardened concrete's mechanical strengths, cracking problems and secondary effects in fluid concretes such as bleeding or segregation of the gravel.

Standards related to the cleanliness of the aggregates for concrete applications therefore exist.

The first standard is a test known as the <<Equivalent Sand: SE>> test (NF EN 933-8 standard). According to this standard a test is done consisting of flocculating the fines of the tested sand in a test tube and comparing the volume of the floes with the total volume of the sediments. The more flocculated fines there are, the more the sand equivalent value decreases and the more the sand is considered to be dirty. This test is nevertheless not sensitive enough to predict future problems in the concrete.

The second test is called the <<Methylene Blue Value: MBV>> (NF EN 933-9 standard). It comprises determining the maximum amount of methylene blue that would adsorb itself on the sand's impurities. Indeed, this dye has a very great affinity for clays, this affinity directly depends on the level of clay in the sand and the nature of the given clays. This test may be simply done by adding <<drop by drop>> (progressive additions of given volumes of the blue solution) the methylene blue in a solution containing sand and making stains with this solution at different time periods on filter paper. The measurement is done on the sand's 0-2 mm fraction, and the current standard imposes one measurement per week at the quarry on sand to be used in concrete applications.

An apparatus called the <<valise de Bleu>> is also known to measure the noxiousness of sand fines (see the NF 18-595 standard). This compact equipment comprises a beaker with an agitator, a peristaltic pump and a spectrophotometric measuring system comprising a measuring cell. The measurement (called turbidimetric) is done on a suspension of sand fines, that is, particles smaller than 80 µm. in size. The principle consists of progressively adding, in the beaker containing this suspension, a solution of methylene blue, then sending it to the cell (by the pump) to measure the absorption, at the 660 nm wave length (corresponding to maximum absorption of the methylene blue), of a light beam crossing the latter. The measurement is done while the solution of methylene blue is added to the suspension. At the beginning of the dosage, the methylene blue is consumed by the clays, therefore it does not reduce the light signal. Then, when the sand's maximum adsorption level is reached, residual blue remains in the solution and the intensity of the spectrophotometric signal drops. The blue value has been reached.

Nonetheless, the above-mentioned methods provide an insufficient control of sand cleanliness, notably due to possible variations of this cleanliness when working at the quarry. Furthermore they have long response times.

A real need to improve the control of sand cleanliness exists as well as to improve the cleanliness of the produced sands.

Resume of the Invention

The invention first of all provides a production process of sand comprising:
  the extraction of sand from a quarry;
  the periodic on-line and automated withdrawal of a sample of sand;
  the automated measurement of the methylene blue value on the sample of sand.

According to one particular embodiment, the automated measurement of the methylene blue value comprises an automated measurement of the methylene blue value in an aqueous solution and/or an automated measurement of the methylene blue value in a mixture of water and di-ethylene glycol.

According to one particular embodiment, depending on the result of the measurement of the methylene blue value, the sand is washed and/or inerted and/or sorted and/or the extraction is modified.

According to one particular embodiment, the sample is taken and the measurement of the methylene blue value is done at least once a week, preferably once a day, more preferably at least once an hour, ideally once approximately every ten minutes.

According to one particular embodiment, the produced sand has a methylene blue value comprised in a predetermined range, the said process comprising:
  the mixture of the sand with an inerting agent.

According to one particular embodiment, the mixture of the sand with an inerting agent is done upstream and/or downstream from the withdrawal of the sample of sand.

According to one particular embodiment, the amount of inerting agent during the mixing is adjusted according to the measurement of the methylene blue value so that the sand from the mixture has a methylene blue value comprised in the predetermined range.

According to one particular embodiment, the inerting agent is selected from among cationic molecules and principally polycationic molecules, principally of the polyamine type, with or without the supplementary addition of polyanionic molecules, the cement's plasticizing agents.

According to one particular embodiment, the above-mentioned process comprises the homogenization and/or screening and/or dividing and/or drying of the sample of sand, before measurement of the methylene blue value.

According to one particular embodiment, the measurement of the methylene blue value comprises:
mixing the sample of sand with a solution to form a dispersion;
the injection of a single dose of methylene blue in the dispersion;
the separation of the dispersion into particles and a liquid fraction; and
the determination, in the liquid fraction, of the excess amount of unreacted methylene blue with the sample of sand.

According to one particular embodiment, the said separation is done by filtering and/or sedimentation by addition of a flocculating agent.

According to one particular embodiment, the determination of the amount of unreacted methylene blue is done by absorbance and/or transmittance measurements.

According to one particular embodiment, the said absorbance and/or transmittance measurements are done in a spectrophotometric cell or using a phototrode.

According to one particular embodiment, the said absorbance and/or transmittance measurements are done at a wave length from 640 to 680 nm and preferably 660 nm.

According to one particular embodiment, the dose of injected methylene blue is between approximately 0.1 and approximately 20 g of dry methylene blue per kg of sand, preferably between 5 and approximately 10 g of dry methylene blue per kg of sand.

The invention also provides a production line of sand comprising:
means for the extraction 1 of sand in a quarry;
means for periodic and automated withdrawals 6 of samples of sand;
means for automated measurements 10 of the methylene blue value on the sample of sand.

According to one particular embodiment, the above-mentioned production line of sand comprises:
means for washing the sand.

According to one particular embodiment, the above-mentioned production line of sand comprises:
means for mixing 4 the sand with an inerting agent, the said mixing means 4 being located upstream and/or downstream from the withdrawal means 6 of the sample of sand.

According to one particular embodiment, the above-mentioned production line of sand comprises a regulatory means 12 between the automated measurements means 10 of the methylene blue value and the mixing means 4 of the sand with an inerting agent.

According to one particular embodiment, the withdrawal means 6 of the sample of sand comprise a rotary traversing sampler or a pivoting traversing sampler or a drawer sampler or an endless screw sampler.

According to one particular embodiment, the above-mentioned production line of sand comprises means for the homogenization and/or screening and/or dividing and/or drying 8 of the sample of sand upstream from the means measurement means 10 of the methylene blue value.

According to one particular embodiment, the measurement means 10 of the methylene blue value comprise:
a mixing receptacle 21 of the sample of sand with a solution and with methylene blue;
means for automated dosage and injection 24 of methylene blue in the mixing receptacle 21.

According to one particular embodiment, the measurement means 10 of the methylene blue value comprise means to filter 27 and/or means to inject the flocculating agent 25.

According to one particular embodiment, the mixing receptacle 21 has a phototrode.

According to one particular embodiment, the above-mentioned production line of sand comprises:
a spectrophotometric measurement cell 29;
means of circulation 26, 28 from the mixing receptacle 21 towards the measurement cell 29 and means of circulation 30 from the measurement cell 29 towards the mixing receptacle 21.

The invention further provides a measurement process of the methylene blue value of a sample of sand, comprising:
mixing the sample of sand with a solution to form a dispersion;
the injection of a single dose of methylene blue in the dispersion;
the separation of the dispersion into particles and a liquid fraction; and
the determination, in the liquid fraction, of the excess amount of unreacted methylene blue with the sample of sand.

This measurement process is specially conceived to be used within the scope of the above-mentioned production process of sand.

According to one particular embodiment, the solution is an aqueous solution or a mixture of water and di-ethylene glycol.

According to one particular embodiment, the said separation is done by filtering and/or sedimentation by addition of a flocculating agent.

According to one particular embodiment, the determination of the amount of unreacted methylene blue is done by absorbance and/or transmittance measurements.

According to one particular embodiment, the said absorbance and/or transmittance measurements are done in a spectrophotometric cell or using a phototrode.

According to one particular embodiment, the said absorbance and/or transmittance measurements are done at a wave length from 640 to 680 nm and preferably 660 nm.

According to one particular embodiment, the dose of injected methylene blue is between approximately 0.1 and approximately 20 g of dry methylene blue per kg of sand, preferably between 5 and approximately 10 g of dry methylene blue per kg of sand. This invention makes it possible to overcome the inconveniences of prior art. It more particularly provides a process to improve the cleanliness control of sand in quarries.

This is accomplished thanks to the development of a production process of sand comprising an integrated, on-line and automated measurement of the sand's methylene blue value.

According to certain particular embodiments, the invention also has the advantageous characteristics enumerated below:
It is possible to control sand cleanliness on the production site much more frequently than currently and in the current standard, and it is simple and economical, essentially without human intervention. The increase of the measurement frequency makes it possible to more closely monitor the evolution of the sand's cleanliness while it is being extracted.
The process, according to the invention, is more reliable and more accurate than existing processes on filter paper or manual spectrophotometric measurements on a suspension of fines.

The embodiment on which an over dosage of methylene blue is done provides a considerable savings of time compared to the <<drop by drop>> addition method of methylene blue.

The measurement of the methylene blue on the sand's production line makes it possible to set up a feedback cycle to produce a sand with a predetermined level of cleanliness, despite possible variations of the quality of the sand produced in the quarry.

The invention also provides a production process of clean sand, inerted on the same production line by adding an active agent specifically reacting on the impurities, notably the clays. The adjustment of the quantities of inerting agent according to the measurement of the methylene bleu value further provides a means to make savings on the inerting products that are expensive Finally, the invention makes it possible to gain in productivity and makes the entire production of sand usable (that is, valuable for a given application). The service lives of quarries are therefore increased.

DESCRIPTION OF EMBODIMENTS OF THE INVENTION

The invention will now be described in more detail and in a non-limiting manner in the description that follows.

Quarry Sand Production Line

Figure 1:
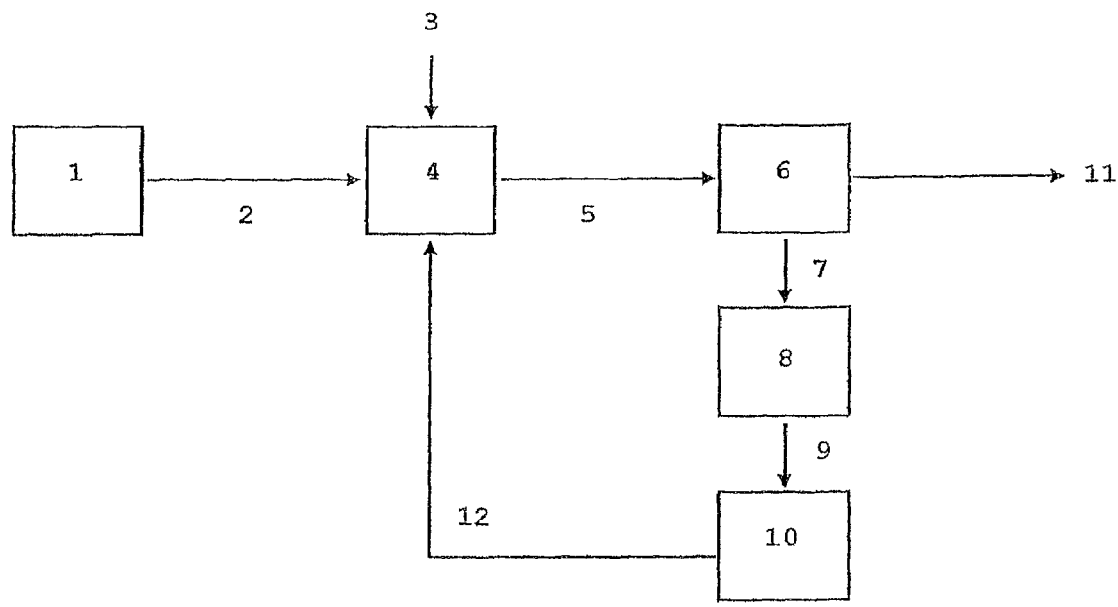
FIG. 1 diagrammatically represents an example of a production line according to the invention.

With reference to FIG. 1, an example of a production line of quarry sand according to the invention comprises means of extraction 1. These means may comprise phases:

extraction from the quarry of massive or alluvial rocks, cleaning to remove mud, screening (sieving), crushing. Means of conveyance 2 of the raw sand (that may comprise conveyor belts, silos, hoppers, chutes, etc) carry the extracted sand towards mixing means 4 of the sand with an inerting agent. The mixing means 4 are, on the other hand, fed by a supply line 3 of the inerting agent. The mixing means 4 of the sand with the inerting agent may comprise a mixer in which the inerting agent is introduced. The latter is preferably sprayed on the sand during the mixing. Any type of mixer may be used. The spray nozzles should be selected according to the desired flow ranges of the inerting agents and to the geometry of the installation. The inerting agent may also be directly added to the material to be treated by simply pouring it if the flow of the material is sufficiently channelled. The treatment is preferably done continuously but it may also be done per batch.

At the output of the mixing means 4, means of conveyance 5 are provided for the inerted sand. On the path of these conveyance means 5 are located means for periodic and automated withdrawals 6 of samples of sand. These withdrawal means 6 are advantageously provided to withdraw a typical amount of sand of at least 200 g, preferably from approximately 200 to approximately 250 g. The withdrawal 6 could require being higher than 250 g to ensure the representativeness of the sample. It could reach several tens of kilograms. To this effect it is possible to use a sampler such as those commercialized by the companies Penox, Tema, Forratechnic. The rotary, linear or pivoting traversing samplers and the conduit sampler guarantee good representativeness of the samples of sand in relation to all the sand on the production line; they limit the problems of segregation related to the heterogeneity of the supply. Nonetheless, other samplers such as the drawer sampler, the endless screw sampler, the flap sampler and the belt sampler may be preferred due to their lower price and their simplicity.

The production line further comprises, downstream from the means of withdrawal 6, means of conveyance 11 of the produced sand that may, for example, feed a sand-conditioning system. Furthermore, at the output of the withdrawal means 6, are provided conveyance means 7 of the sample of sand. These conveyance means 7 feed the treatment means 8 of the sample of sand. These treatment means 8 may comprise, depending on the case, means of homogenization and/or screening and/or dividing and/or drying. The homogenization means comprise, for example, a mixer. The screening means comprise, for example, a sieve. The dividing means comprise, for example, quartering systems. These may be simple quartering systems by gravity or automatic, preferably rotary quartering devices. The drying means comprise, for example, heating means. All the withdrawal means 6 and the treatment means 8 may be integrated in a same apparatus, in which case the conveyance means 7 are limited to a bare minimum and even absent.

At the output of the treatment means 8 conveyance means are provided 9 for the treated sample that feed the automatic measurement means 10 of the methylene blue value. A regulatory means 12 is provided that makes it possible to adjust the operating parameters of the sand's mixing means 4 with the inerting agent according to the result of the measurement of the methylene blue value obtained at the level of the automatic measurement means 10.

The position of the mixing means 4 upstream from the withdrawal means 6 is optional. It is also possible that the mixing means 4 be located downstream from the withdrawal means 6. According to this variant, the withdrawal means 6 are located directly on the path of the conveyance means 2 of the extracted sand. Then, downstream from the withdrawal means 6 are located the mixing means 4. The regulatory means 12 between the automated measurement means 10 and the mixing means 4 may also be present in this variant. A third possibility comprises combining the two variants, providing a first mixing means of the sand with an inerting agent upstream from the withdrawal means and a second mixing means of the sand with an inerting agent downstream from the withdrawal means.

According to another variant of the production line it is possible to replace the mixing means 4 of the sand with an inerting agent by washing means of the sand, that may comprise a washer to remove mud and/or one or several separation systems of the dirty water and the sand (sieve, cyclone, filtering systems, etc). It is equally possible to use mixing means in combination with washing means.

According to another, more simple variant of the production line according to the invention, the mixing means 4 of the sand with an inerting agent are simply omitted.

The production line according to the invention is, for example, adapted to a production of sand within the range of 150 tons an hour. The sand flow is not a limiting parameter.

Quarry Sand Production Process

In the production process of quarry sand according to the invention, sand is extracted from the quarry using extraction means I and carried by conveyance means 2. The given sand is comprised of aggregates with an average size from 0 to 20 mm, preferably from 0 to 4 mm. It may be of any mineral, calcareous, siliceous, siliceous-calcareous or other nature. It may comprise from approximately 0 to 5% in mass of clay.

At a certain location on the production line (before and/or after the washing and/ or inerting process), a sample of sand is withdrawn in a periodic and automated manner.

Periodic withdrawal is understood as samples of sand being successively and repeatedly withdrawn. It may be a withdrawal at regular time intervals, for example once a week or once a day or once an hour, even once every ten minutes and even more frequently. The duration of the withdrawal may also be variable, from a few seconds to several minutes. It may also be a withdrawal an irregular time intervals. For example, the frequency of the withdrawals may be reduced if the sand has relatively homogeneous and constant characteristics or, on the contrary, the withdrawal frequencies may be increased if the quality of the sand shows important variations.

An automated measurement of the methylene blue value is then done on the sample of sand. The sample of sand may optionally be treated before carrying out this measurement.

Hence, it may be opportune to screen (sieve) the sample before the measurement. It could indeed be only necessary to make the measurement on a fraction of the sand, for example, on the 0-2 mm of the sand, in order to conform to the standards in force. In this case, the sample of sand is sieved and only the passing part is kept. Typically, approximately 30% of the mass of the sample is removed, corresponding to the 2-4 mm fraction. A drying operation is done on the sample before the screening may be carried out. This will be all the more necessary when the sand is dirty, humid and the clay is sticky.

Furthermore, it may be opportune to divide the sample of sand before the measurement. The measurement should indeed be done on a predetermined mass of sand, for example, from approximately 200 to approximately 250 g, more particularly approximately 225 g. It is possible to provide that the withdrawal means and optionally the screening means be adapted to provide a sample with a desired mass. Otherwise, the sample is divided in such a way as to conserve its representativeness.

Finally, if the sample of sand is humid, it may be opportune to dry it before the measurement. This drying operation may, for example be done by setting up a heated bowl or a heated homogenization system at approximately 100° C. Alternatively, it is possible to do the measurement on the humid sand directly, which imposes the need to take the humidity into account in the calculation of the methylene blue value of the raw sand.

The automated measurement of the methylene blue value is then done, as described below. The aim of the result of this measurement may be to simply have precise information on the cleanliness level of the produced sand, and to control the quality of the sand. But the result of the measurement may also make it possible to adapt the production parameters of the sand, either by a human intervention, or in an integrated and automated manner. If the result of the measurement reveals that the sand in not clean enough (a higher methylene blue value than the determined value) it would be possible to:

to sort the sand, so as to discard the sand in the production that is not clean enough, or at least allot it to a specific final utilization (less demanding in terms of quality); or modify the extraction, for example, by changing the quarry face; or carry out a certain number of operations on the sand in order to improve its cleanliness and its quality, for example, in order to do what is necessary for its methylene blue value to return below the determined value.

In this last case, the production process of sand comprises a regulatory means (and possibly a feedback cycle). It is therefore possible, according to this embodiment to produce a quarry sand that has a methylene blue value comprised within a (given) predetermined range, and hence produce a sand with predetermined levels of cleanliness and quality. This regulatory means may operate in an automated manner.

The operations likely to improve the cleanliness of the sand are mainly the washing operation (with water or an aqueous solution), for which the duration and intensity may be adapted according to the measurement of the methylene blue value and the inerting operation.

By inerting is understood the neutralization of such impurities as clays. The inerting process is done by mixing the sand with an inerting agent that should specifically react with the clays. Appropriate inerting agents are those described in the FR 2875496 document (French patent application FR 04/09968) as well as the French patent applications FR 05/06596 and FR 05/06594, filed by the Applicant.

The particular inerting agent used may be a cationic polymer. The inerting agent is advantageously selected from among the cationic molecules containing quaternary ammonium, principally polycationic, principally of the polyamine type, in particular the FL2250 (SNF). The inerting agent may equally comprise a co-mixture of cationic and anionic molecules, the latter being plasticizing agents for cement.

The inerting process of the sand may be done by a simple mixture of the sand with the inerting agent. The dose of injected inerting agent may vary from 0 to 1% of dry inerting agent in the sand and preferably from 0 to 1 g of dry inerting agent/kg of sand. This dose is preferably adapted according to the result of the automatic measurement of the methylene blue value, in order to provide an inerted sand whose methylene blue value is lower than a specified value.

The treatment of the sand by the washing and/or inerting process may be done downstream from the withdrawal of the sample. In this case, the inerting process corrects the cleanliness of the produced sand according to the cleanliness of the raw sand that came from the quarry. The amount of inerting agent to be added to obtain a given methylene blue value should also be adapted according to the nature of the sand and more precisely to the nature of the clays found in the sand.

In the case of sands containing a lot of clays it is possible to provide a first treatment by the washing and/or inerting process immediately after the extraction, then a withdrawal of the sample and a measurement of the methylene blue value to control whether the treated sand provides a satisfactory level of cleanliness and then, only if it is considered necessary, a second treatment by the washing and/or inerting process to finish improving the sand's cleanliness level.

It is also possible to decide that the sand will be submitted to only one treatment by the washing and/or inerting process immediately after the extraction and upstream from the withdrawal of the sample. This configuration has a double advantage of (i) providing a real measurement of the methylene blue value of the finally produced and commercialized sand, and (ii) providing, despite everything, an adjustment of the treatment (notably an adjustment of the dose of the inerting agent) of the future extracted sand, according to the result of this measurement. This configuration is particularly well adapted to quarries in which the extracted sand presents slow-enough drifts in terms of quality to be corrected within a certain lapse of time.

The sand produced by the process according to the invention may be used to make concrete or to make bitumen, for example.

Specific Device and Process for Measurement of the Methylene Blue Value

Figure 2:
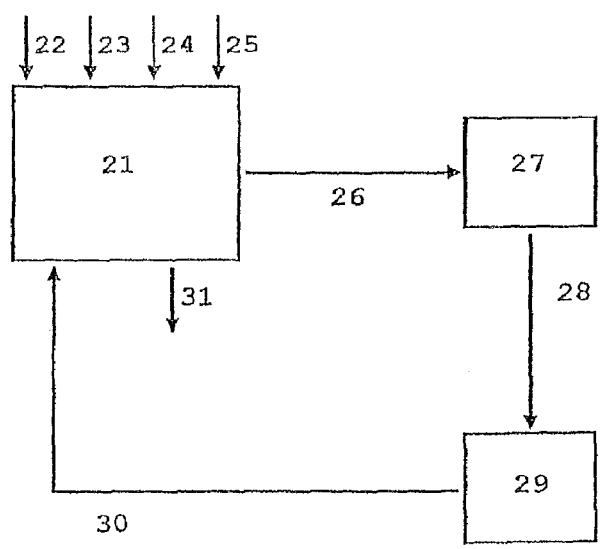
FIG. 2 diagrammatically represents an example of an automated measurement device of the methylene blue value that is integrated on the production line according to the invention.

With reference to FIG. 2, an example of automated measurement means 10 of the methylene blue value comprises a mixing receptacle 21 provided with stirring means, fed by an automatic dosage and injection line 22 of the sample of sand, an automatic dosage and injection line 23 of water (or aqueous solution) and an automatic dosage and injection line 24 of methylene blue. The mixing receptacle 21 may also comprise an automatic dosage and injection line 25 of flocculating agent. A first withdrawal line 26 connects the mixing receptacle 21 to the filtering means 27. A second withdrawal line 28 connects the filtering means 27 to a spectrophotometric cell 29. A third withdrawal line 30 connects the spectrophotometric cell 29 to the mixing receptacle 21. The mixing receptacle 21 is advantageously provided with a draining system 31.

Alternatively, it is possible to not use the lines 26, 28, 30 and the spectrophotometric cell 29 and replace everything with a phototrode directly located in the mixing receptacle 21 (or in an appendant receptacle communicating with the mixing receptacle 21).

The measurement process is carried out as follows: the pre-treated sample of sand (that is, sieved and/or divided and/or dried) is introduced by the line 22 in the mixing receptacle 21. It is mixed under agitation with water or an aqueous solution coming from the line 23, to provide a dispersion (or suspension). A dose of methylene blue is then injected by the line 24, and the dispersion is again mixed. The injected methylene blue then reacts, entirely or partially, with the clay impurities in the sand. It is then time to measure whether excess unreacted methylene blue remains, and if yes, what quantity. To do this a photometric measurement is carried out by absorbance and/or by transmittance.

A first means of doing this photometric measurement comprises having the dispersion circulate up and into the spectrophotometric cell 29 where the absorption and/or the transmission of a light beam through the cell is measured. The dispersion may circulate again returning to the mixing receptacle 21.

A second means of doing this photometric measurement comprises using a phototrode. This entails having done prior calibration with the various solutions of methylene blue at different concentrations.

In both cases, it is generally necessary to do the effective measurement on a relatively clear liquid phase, which implies a separation step of the dispersion into a liquid phase and into particles. This step is an additional difficulty compared to the process known as the <<Valise de Bleu>> process, where the sample of sand is a very diluted sample of fines with a diameter lower than 80 µm, to such an extent that the measurement is less disturbed by the presence of particles, which reduce the signal.

This separation may be, for example, done by sedimentation or by filtering using filtering means 27, which may comprise a filter or several filters in a series (for example first a rough filtering and then a fine filtering process). It is also possible, as a complement or in replacement of filtering means 27, to provide centrifugation means. The mixing receptacle 21, itself may optionally be directly centrifuged. A third method that may be used as a complement or in replacement of the two previous methods is flocculation. The injection of a flocculating agent by the line 25 does indeed make it possible to sediment the finest particles of the dispersion in a few minutes and generally in a few seconds, the larger fines rapidly settle under the effect of their own weight. The flocculating agents are selected from among the usually-used products in the aggregates industry to flocculate sand fines in loaded water after washing of the materials. Generally, the non-ionic or cationic flocculants are preferred because they present a lower risk of reacting with the methylene blue's cationic molecule. As examples of a flocculating agent used here, the following can be mentioned: Praestol 2300D (DEGUSSA), FA920 (SNF) and AN905 (SNF). In all events the filters or flocculating agent are selected in such a manner that they are efficient for the type of sand and clays in play and that they do not interact with the methylene blue.

The dosage of dry flocculating agent is generally from 0.1 to 100 ppm and preferably from 1 to 20 ppm.

The injection of methylene blue may be carried out several times, by repeating the above operation and with a photometric measurement after each injection until determination of the methylene blue value, in a similar manner to what is known within the scope of the turbidimetric method (cf. P18-595 standard). But it is also possible to be satisfied with one photometric measurement, as long as an over dosage of methylene blue is made, that is, to inject a unique dose of methylene blue in excess compared to the amount necessary to react with the sand's clays, and to then directly measure the amount of methylene blue that reacted and hence the methylene blue value (equal to the amount in g of adsorbed methylene blue per kg of sand). For example the single dose of methylene blue may be between 0.1 and 20 g of methylene blue per kg of sand and preferably between 5 and 10 g per kg of sand and may be more precisely selected according to the range of cleanliness expected for a given sand. For example, an amount of 1 g of methylene blue for 250 g of sand could be appropriate if the sand's blue value is still below 4 g per kg of sand.

Given that the photometric measurement is therefore done on a dispersion that appears to be saturated in methylene blue, and given the sensitivity of the measurement apparatus, it may be useful or necessary to make several measurements and notably:

- to dilute the dispersion before the measurement in such a way that the concentration of methylene blue in the dispersion remains within the range of several ppm maximum (typically less than 10 ppm for a measurement with a spectrophotometer or less than 5 ppm with a phototrode) and/or
- carry out absorbance calibrations rather than transmittance calibrations, because transmittance is proportional to the measured light intensity while absorbance varies with the logarithm of the measured light intensity (this typically makes it possible to broaden the range of measurable concentrations from 0-4 ppm to 0-8 ppm) and/or
- to either work using a light beam with a wave length from 640 and 680 nm, preferably 660 nm (which corresponds to the maximum absorption value of methylene blue) or rather work on an offset wave length compared to the absorption peak, for example at a wave length of approximately 590 nm, in order to reduce the sensitivity of the measurement.

The measurement method by over dosage offers a considerable savings of time compared to the <<drop by drop>> method (progressive additions of volumes of the blue solution). The measurement process of the methylene blue value for a sample of sand described here is specially adapted to be used within the scope of the production process of sand according to the invention and to be implemented on the production line of the invention. But this measurement process may also be used independently, for example to carry out laboratory tests.

At the end of the automated measurement, the system should be cleaned in view of receiving the next sample. Notably, the mixing receptacle 21 should be drained by the line 31, and optionally washed with water thanks to the line 23.

Specific Measurement of the Methylene Blue Value in a Mixture of Water/Di-ethylene Glycol (Notably 50/50 in Mass)

For complementary information on this measurement method it is possible to refer to A.I.G. Yool and coll., *Cement and Concrete Research*, Vol. 28, n°10, pp 1417-1428, 1998.

According to one variant of the invention, it is possible to determine the absorption capacity of a sand, in terms of methylene blue, no longer in water, but in a mixture containing water and di-ethylene glycol, notably 50% mass of water and 50% mass of di-ethylene glycol. This new value is known as $MBV_{DEG}$.

The current inventors have shown that the $MBV_{DEG}$ is almost equal to the standard blue value (EN NF 933-9 standard) in the case where the sand contains non-swelling clays (illite, kaolinite, etc), but that it greatly decreases (by a factor close to 2) when the sand contains swelling clays.

By determining calibration curves with different natures of clays, and measuring the difference between the standard blue value (MBV) and the $MBV_{DEG}$, it is possible to evaluate the level of swelling clays in a sand that would have been submitted to the two measurements.

By considering the average variation of the standard blue values for each nature of clay according to their level, it is also possible to calculate an approximate level of the sand's non-swelling clay. The evaluations of the levels of clay may be improved by good knowledge of the sand's deposits and the clays polluting them. It is therefore possible to select the calibration curves corresponding to the clays found in majority on each site.

This method with di-ethylene glycol may be used within the scope of this invention by adding an automatic dosage and injection line of di-ethylene glycol in the mixing receptacle 21. The use within the scope of the invention of a measurement of methylene blue in water or an aqueous solution (MBV) and a measurement of the methylene blue in a mixture of water/di-ethylene glycol ($MBV_{DEG}$) makes it possible to estimate the levels of various natures of clay in the sand.

If the two measurements are to be done simultaneously, MBV and $MBV_{DEG}$, two automatic apparatus are necessary on the line. The withdrawal system is consequently adapted.

EXAMPLES

The following examples illustrate the invention without limiting it.

Example 1

Measurement of the Methylene Blue Value by Over Dosage

The measurements of the methylene blue value by over dosage are done using a phototrode (Phototrode™ DP5 (METTLER-TOLEDO)).

The phototrode is calibrated beforehand with aqueous solutions of methylene blue at 0, 0.5, 1, 1.5, 2, 3 and 4 mg/L (measured tension from respectively approximately 1500 mV and approximately 130 mV).

The measurement protocol is the following:
1) Weighing of 200 to 250 g of 0-2 mm sand and installation in a beaker.
2) Addition of 500 mL of water.
3) Agitation of the suspension.
4) Addition of 100 g of a solution of methylene blue at 10 g/L using a precision doser.
5) Agitation of the suspension.
6) Pumping of a few mL of the suspension into a tube.
7) Centrifugation for several minutes at 4500 revolutions/min.
8) Recuperation of the supernatant and dilution of 100 µL of the supernatant in 100 mL of water (dilution at 1/1000).
9) Installation of the phototrode in the solution and spectrophotometric measurement.
10) Calculation of the sand's methylene blue value (equal to the quantity in g of adsorbed methylene blue per kg of sand).
11) Automatic cleaning of the phototrode.
12) Draining and cleaning of the beaker.

An example of measurement results for different samples of sand numbered from 1 to 6 (calcareous sand 0-4 mm from the Lafarge Estaque quarry/Bouches du Rhône,) is summarized in table 1 below.

TABLE 1

Results of the measurements of the methylene blue value by over dosage

| Sample | Phototrode Signal | Absorbance | Concentration of methylene blue in the dilution | Value of methylene blue (g/kg sand) |
|---|---|---|---|---|
| 250 g sand1: washed sand | 530 mV | 0.452 | 1.66 ppm | 0.00 |
| 250 g sand 2 | 626 mV | 0.380 | 1.40 ppm | 0.64 |
| 250 g sand 3 | 750 mV | 0.301 | 1.11 ppm | 1.34 |
| 250 g sand 4 | 958 mV | 0.195 | 0.72 ppm | 2.27 |
| 250 g sand 5 | 1315 mV | 0.057 | 0.21 ppm | 3.50 |
| 250 g sand 6: MBV* = 5 | 1501 mV | 0.000 | 0 ppm | >4.00 |

*Methylene blue value obtained following the NF EN 933-9 standard.

Furthermore, in order to validate that this methylene blue value measured by this method is the same as the methylene blue value obtained by a traditional method, parallel tests were done with the stain method (NF EN 933-9) and with the above method of spectrophotometric measurement by over dosage.

These tests were done using samples of very clean sand (0-4 mm calcareous sand from the Lafarge Estaque quarry, washed in the laboratory, dried at 105° C., then sieved at 2 mm), to which clays were added, that is, respectively 1% of montmorillonite (blue montmorillonite from Sardinia (SOCODIS)), 2% of illite (illite from Le Puy (SOCODIS)) and 3% of kaolinite (kaolinite type BS3 (AGS)). The results are summarized in table 2 below and show the reliability of the over dosage method. It should be noted that the MBVs are measured on the 0-2 mm fraction of the sand but related to the total sand=$MBV_{0-4}$.

TABLE 2 comparison of the methylene blue value measured by the stain test or by over dosage

| Sample | $MBV_{0-4}$ (stain test) (g blue/kg 0-4 mm sand) | $MBV_{0-4}$ (measurement by over dosage) (g blue/kg 0-4 mm sand) |
|---|---|---|
| Sand + montmorillonite | 1.9 | 1.84 |
| Sand + illite | 1.2 | 1.12 |
| Sand + kaolinite | 0.8 | 0.80 |

In another test, flocculants were used to facilitate the necessary filtering phase of the suspension of sand before the measurement with the phototrode. The results, summarized in the following table 3, show that the blue value of a sand polluted by a mixture of 3 different clays is not affected by the presence of selected flocculants.

These tests were done on the 0-2 mm fraction of samples of very clean sand (0-4 mm calcareous sand from the Lafarge Estaque quarry, washed, at the laboratory and dried at 105° C.), to which a mixture of clays was added (0.95% of montmorillonite (blue montmorillonite from Sardinia (SOCODIS))+1.9% of illite (illite from Le Puy(SOCODIS)) +1.9 % of kaolinite (kaolinite type BS3 (AGS)).

TABLE 3 comparison of the methylene blue value measured by the stain test with and without a flocculant

| Mass of clay sand | Type of flocculant | Concentration of flocculant | Methylene blue (g/kg sand) |
|---|---|---|---|
| 257.2 g | None | 0 ppm | 3.4 |
| 257.2 g | Praestol 2300D (DEGUSSA) | 20.00 ppm | 3.4 |
| 257.2 g | FA 920 (SNF) | 20.00 ppm | 3.4 |
| 257.2 g | AN 905 (SNF) | 6.00 ppm | 3.1 |
| 257.2 g | AN 905 (SNF) | 12.00 ppm | 3.3 |
| 257.2 g | AN 905 (SNF) | 20.00 ppm | 3.2 |

Example 2

Regulation of a Sand's Methylene Blue Value

In order to be able to efficiently regulate the methylene blue value of a sand (hence its cleanliness), it is necessary to approximately know the nature of the clays it contains.

By carrying out various experiments that reduce the methylene blue value of a clean sand to which is added a given quantity of clay of a certain nature, and this, using a given inerting agent, it is possible to calculate the aptitude of this inerting agent to reduce by one unit the value of methylene blue according to the nature of the clay.

For example, for the inerting agent FL2250 (SNF), it was calculated that the proportion of dry inerting agent, as related to the sand needed to reduce the value of methylene blue by one unit, is:

480 ppm for the pure montmorillonite pure (75% in the blue montmorillonite from Sardinia);
690 ppm for the pure illite (85% in the illite from Le Puy);
680 ppm for the pure kaolinite (90% in the kaolinite type BS3).

In the case of mixtures of clays, it was highlighted that the FL2250 has a higher affinity to the swelling type of clay (montmorillonite), in such a way that the inerting agent first neutralizes this swelling clay before neutralizing, if it is in sufficient quantity, the non-swelling clays.

Example 3

Utilization of the Methylene Blue Value in a Solution of Di-Ethylene Glycol to Evaluate the Amounts of Various Natures of Clays in a Sand The aim of this example is to show how the evaluation of the level of swelling clays on one hand and non-selling clays on the other is done.

The calculation is based on the difference of the methylene blue value between one standard measurement (NF EN 933-9 standard) and a stain measurement, done strictly in the same manner in a mixture of water and di-ethylene glycol at 50% in mass.

The materials used are samples of very clean sand (0-4 mm calcareous sand from the Lafarge Estaque quarry, washed at the laboratory, dried at 105° C. then sieved at 2 mm), to which clays are added (blue montmorillonite from Sardinia (SOCODIS) containing 75% of pure montmorillonite or the kaolinite type BS3 (AGS) containing 90% of pure kaolinite).

The obtained results are summarized in table 4. It should be noted that the MBVs are measured on the 0-2 mm fraction of the sand but related to the total sand=$MBV_{0-4}$.

TABLE 4 comparison of the methylene blue values measured in water and in a solution of di-ethylene glycol in the presence of different natures of clays

| Sample | $MBV_{0-4}$ (g blue/ kg 0-4 mm) sand | $MBV_{DEG\ 0-4}$ (g blue/ kg 0-4 mm sand) | Difference bewteen the two values |
|---|---|---|---|
| Washed 0-4 mm sand | 0 | 0 | 0 |
| Washed 0-4 mm sand + 1% pure montmo. | 2.65 | 1.3 | 1.35 |
| Washed 0-4 mm sand + 2% pure montmo. | 5.2 | 2.55 | 2.65 |
| Washed 0-4 mm sand + 3% pure montmo. | 8.0 | 4.0 | 4.00 |
| Washed 0-4 mm sand + 2% pure kaol. | 0.60 | 0.43 | 0.17 |
| Washed 0-4 mm sand + 4% pure kaol. | 1.19 | 0.86 | 0.33 |
| Washed 0-4 mm sand + 6% pure kaol. | 1.82 | 1.31 | 0.51 |

On the one hand the values of methylene blue of sands containing swelling clays of the montmorillonite type are shown to be much greater than those of non-swelling clays such as kaolinite, and on the other hand the differences between the blue values in water and in the solution of di-ethylene glycol are shown here to be much greater for the swelling clays (approximate factor equal to 16 for an identical level of impurities).

The following Table 5 gives the measurements done on clean sand intentionally-polluted by mixtures of pure clays. Two samples of industrial sands from the Estaque quarry were also analyzed.

TABLE 5

Measurements of methylene blue in water or in a solution of Di-ethylene Glycol for intentionally-polluted sands or industrial sands

| Sand | $MBV_{0-4}$ (g blue/ kg 0-4 mm sand) | $MBV_{DEG\ 0-4}$ (g blue/ kg 0-4 mm sand) | Difference between the two values |
|---|---|---|---|
| Washed 0-4 mm sand + 1% de montmo. pure + 1% de kaolinite pure | 2.95 | 1.5 | 1.45 |
| Washed 0-4 mm sand + 2% pure montmo. + 2% pure kaolinite | 5.9 | 3.05 | 2.85 |
| Sand 7 | 2.0 | 1.0 | 1.0 |
| Sand 8 | 4.2 | 2.4 | 1.8 |

The first stage of the calculation consists of using the results of table 5 and considering that the difference between the blue values in the water and in the solution of di-ethylene glycol is completely due to the swelling clay. The results are summarized in the following table 6.

TABLE 6

Evaluation of the level of swelling clays in intentionally-polluted sands or industrial sands

| Sample | Difference between the $IBV_{0-4}$ and the $MBV_{DEG\ 0-4}$ | Level of swelling clays (%/0-4 mm sand) |
|---|---|---|
| Washed 0-4 mm sand + 1% pure montmo. + 1% pure kaol. | 1.45 | 1.05 |
| Washed 0-4 mm sand + 2% pure montmo. + 2% pure kaol. | 2.85 | 2.1 |
| Sand 7 | 1.0 | 0.75 |
| Sand 8 | 1.8 | 1.35 |

The second stage consists of using the results of table 6 (level of swelling clays) and those of table 4 (MBV per nature of clay and related to their level). This then involves calculating the contribution of swelling clays in the sand's methylene blue value and attributing the difference between the sand's MBV and the swelling clays' MBV to the non-swelling clays' MBV. The following table 7 gives the obtained results.

TABLE 7

Evaluation of the level of non-swelling clays in intentionally-polluted sand or industrial sands (first calculation)

| Sample | Level of swelling clays (%/0-4 mm sand) | $MBV_{0-4}$ due to the swelling clays | $MBV_{0-4}$ due to the non-swelling clays | Level of non-swelling clays (%/0-4 mm sand) |
|---|---|---|---|---|
| Washed 0-4 mm sand + 1% pure montmo. + 1% pure kaol. | 1.05 | 2.85 | 0.1 | 0.35 |
| Washed 0-4 mm sand + 2% pure montmo. + 2% pure kaol. | 2.1 | 5.6 | 0.3 | 1.0 |
| Sand 7 | 0.75 | 1.95 | 0.05 | 0.1 |
| Sand 8 | 1.35 | 3.55 | 0.65 | 2.2 |

The results obtained after this first calculation show that the evaluation is perfectly acceptable for the swelling clays (the most noxious for concretes). The estimation, however, of the levels of non-swelling clays is not as good.

It should be noted that the difference of the blue values in the water and in the solution of di-ethylene glycol, for the non-swelling clays is not strictly nil, a series of successive iterations was done to minimize the differences and fine-tune the calculation. The approach involved taking the first evaluation of the levels of non-swelling clays and then calculating the corresponding <$MBV_{0-4}$-$MBV_{DEG\ 0-4}$>> difference, then subtracting it from the actually measured difference for evaluation of the level of swelling clays. The calculation then continues as explained page 19. The results of the first iteration are given in the following table 8 and table 9.

TABLE 8

Calculation of the evaluation of the level of non-swelling clays in intentionally-polluted sands or industrial sands (first iteration)

| Sample | Level of non-swelling clays from the first calculation (%/0-4 mm sand) | Difference between $MBV_{0-4}$ and $MBV_{DEG\ 0-4}$ Due to the non-swelling clays | Difference between $MBV_{0-4}$ and $MBV_{DEG\ 0-4}$ Due to the swelling clays (iteration 1) |
|---|---|---|---|
| Washed 0-4 mm sand + 1% pure montmo. + 1% pure kaol. | 0.35 | 0.03 | 1.42 |
| Washed 0-4 mm sand + 2% pure montmo. + 2% pure kaol. | 1.0 | 0.08 | 2.77 |
| Sand 7 | 0.1 | 0.01 | 0.99 |
| Sand 8 | 2.2 | 0.19 | 1.61 |

TABLE 9

Evaluation of the level of non-swelling clays in intentionally-polluted sands or industrial sands (after the first iteration)

| Sample | Level of swelling clays (%/0-4 mm sand (iteration 1) | $MBV_{0-4}$ due to the swelling clays (iteration 1) | $MBV_{0-4}$ due to the non-swelling clays(iteration 1) | Level of non-swelling clays (%/0-4 mm sand) (iteration 1) |
|---|---|---|---|---|
| Washed 0-4 mm sand + 1% pure montmo. + 1% pure kaol. | 1.05 | 2.8 | 0.16 | 0.5 |
| Washed 0-4 mm sand + 2% pure montmo. + 2% pure kaol. | 2.05 | 5.45 | 0.47 | 1.55 |
| Sand 7 | 0.75 | 1.95 | 0.06 | 0.2 |
| Sand 8 | 1.20 | 3.15 | 1.03 | 3.4 |

The iterations are continued until the difference between the estimations of the levels of clay is minimum. The results obtained after 5 or 6 iterations are summarized in the following table 10.

TABLE 10

Evaluation of the level of non-swelling lays in intentionally-polluted sands or industrial sands (after 6 iterations)

| Sample | Level of swelling clays (%/0-4 mm sand) | Level of non-swelling clays (%/0-4 mm sand) |
|---|---|---|
| Washed 0-4 mm sand + 1% pure montmo. + 1% pure kaol. | 1.05 | 0.75 |
| Washed 0-4 mm sand + 2% pure montmo. + 2% pure kaol. | 2.0 | 2.15 |
| Sand 7 | 0.7 | 0.25 |
| Sand 8 | 1.05 | 4.75 |

As these estimations show, the levels of non-swelling clays have notably improved as one finds almost the same concentrations of clays introduced in the polluted reference sands.

The invention claimed is:

1. A production process of sand, comprising:
extracting sand from a quarry;
performing a periodic, on-line and automated withdrawal of a sample of sand;
performing an automated measurement of the methylene blue value on the sample of sand,
wherein the produced sand has a methylene blue value comprised within a predetermined range, the process comprising mixing the sand with an inerting agent, and
wherein the quantity of inerting agent for the mixture is adjusted according to the measurement of the methylene blue value and in such a way that the sand from the mixture has a methylene blue value comprised within the predetermined range.

2. A production line of sand, comprising:
means of extraction of sand from a quarry;
means of periodic automated withdrawal of a sample of sand;
means of automated measurement of the methylene blue value on the sample of sand
means of mixing sand with an inerting agent, the mixing means being located upstream and/or downstream from the withdrawal means of the sample of sand, and
a regulatory means between the automated measurement means of the methylene blue value and the mixing means of the sand with an inerting agent.

3. A production process of sand comprising:
extracting sand from a quarry;
performing a periodic, on-line and automated withdrawal of a sample of sand;
performing an integrated, online and automated measurement of the methylene blue value on the sample of sand.

4. The process according to claim 3, wherein the automated measurement of the methylene blue value comprises an automated measurement of the methylene blue value in an aqueous solution and/or an automated measurement of the methylene blue value in a mixture of water and di-ethylene glycol.

5. The process according to claim 3, wherein the withdrawal of the sample and the measurement of the methylene blue value are done at least once a week.

6. The process according to claim 3, wherein the produced sand has a methylene blue value comprised within a predetermined range, the process comprising:
mixing the sand with an inerting agent.

7. The process according to claim 6, wherein the mixture of the sand with an inerting agent is done upstream and/or downstream from the withdrawal of the sample of sand.

8. The process according to claim 6, wherein the inerting agent is selected from the group consisting of cationic molecules and mainly polycationic molecules, and polyanionic molecules.

9. The process according to claim 6, comprising homogenizing and/or screening and/or dividing and/or drying the sample of sand, prior to the measurement of the methylene blue value.

10. The process according to claim 3, wherein the measurement of the methylene blue value comprises:
mixing the sample of sand with a solution to form a dispersion;
injecting a single dose of methylene blue in the dispersion;
separating the dispersion into particles and a liquid fraction; and
determining, on the liquid fraction, the excess amount of unreacted methylene blue with the sample of sand.

11. The process according to claim 10, wherein the separation of the dispersion is done by filtering and/or sedimentation by addition of a flocculating agent.

12. The process according to claim 10, wherein the determination of the quantity of unreacted methylene blue is done by an absorbance and/or transmittance measurement.

13. The process according to claim 12, wherein the absorbance and/or transmittance measurement is done in a spectrophotometric cell or using a phototrode.

14. The process according to claim 12, wherein the absorbance and/or transmittance measurement is done at a wave length from 640 to 680 nm.

15. The process according to claim 10, wherein the dose of injected methylene blue is between approximately 0.1 and approximately 20 g of dry methylene blue per kg of sand.

16. A production line of sand comprising:
means of extraction of sand from a quarry;
means of periodic automated withdrawal of a sample of sand;
means of integrated, online and automated measurement of the methylene blue value on the sample of sand.

17. The production line of sand according to claim 16, comprising:
means for washing the sand.

18. The production line according to claim 16, comprising:
means of mixing sand with an inerting agent, the mixing means being located upstream and/or downstream from the withdrawal means of the sample of sand.

19. The production line according to claim 16, wherein the withdrawal means of the sample of sand comprise a rotary traversing sampler or a pivoting traversing sampler or a drawer sampler or an endless screw sampler.

20. The production line according to claim 16, comprising means of homogenization and/or screening and/or dividing and/or drying the sample of sand upstream from the means of measurement of the value of methylene blue.

21. The production line according to claim 16, wherein the measurement means of the methylene blue value comprise:
a mixing receptacle of the sample of sand with a solution and with the methylene blue; and
automated dosage and injection means of the methylene blue in the mixing receptacle.

22. The production line according to claim 21, wherein the mixing receptacle is provided with a phototrode.

23. The production line according to claim 21, comprising:
a spectrophotometric measurement cell;
means of circulation from the mixing receptacle towards the measurement cell and means of circulation from the measurement cell towards the mixing receptacle.

24. The production line according to claim 16, wherein the measurement means of the methylene blue value comprise filtering means and/or means of injecting a flocculating agent.

25. A process of measurement of the methylene blue value on a sample of sand comprising:
mixing the sample of sand with a solution to form a dispersion;
injecting a dose of methylene blue in the dispersion, the dose being in excess compared to an amount of methylene blue that is needed to react with the entire sample of sand;
separating the dispersion into particles and a liquid fraction; and
determining, in the liquid fraction, an excess amount of unreacted methylene blue with the sample of sand.

26. The process according to claim 25, wherein the solution is an aqueous solution or a mixture of water and di-ethylene glycol.

27. The process according to claim 25, wherein the separation of the dispersion is done by filtering and/or sedimentation by addition of a flocculating agent.

28. The process according to claim 25, wherein the determination of the quantity of unreacted methylene blue is done by an absorbance and/or transmittance measurement.

29. The process according to claim 28, wherein the absorbance and/or transmittance measurement is done in a spectrophotometric cell or using a phototrode.

30. The process according to claim 28, wherein the absorbance and/or transmittance measurement is done at a wave length from 640 to 680 nm.

31. The process according to claim 25, wherein the dose of injected methylene blue is between approximately 0.1 and approximately 20 g of dry methylene blue per kg of sand.

32. The process according to claim 25, wherein the dose is in excess compared to the amount of methylene blue that is needed to react with the sand's clays present in the sample.

\* \* \* \* \*